(12) United States Patent
Opie et al.

(10) Patent No.: US 7,831,297 B2
(45) Date of Patent: Nov. 9, 2010

(54) GUIDE WIRE TORQUE DEVICE

(75) Inventors: John C. Opie, Scottsdale, AZ (US);
Stephen J. Joyce, Phoenix, AZ (US)

(73) Assignee: Scottsdale Medical Devices, Inc.,
Scottsdale, AZ (US)

( * ) Notice: Subject to any disclaimer, the term of this patent is extended or adjusted under 35 U.S.C. 154(b) by 1063 days.

(21) Appl. No.: 10/444,773

(22) Filed: May 24, 2003

(65) Prior Publication Data

US 2004/0236214 A1 Nov. 25, 2004

(51) Int. Cl.
*A61B 5/00* (2006.01)
*A61M 25/00* (2006.01)

(52) U.S. Cl. ..................... 600/434; 600/585
(58) Field of Classification Search ............... 600/434, 600/585
See application file for complete search history.

(56) References Cited

U.S. PATENT DOCUMENTS

| | | | |
|---|---|---|---|
| 4,211,233 A | 7/1980 | Lin | |
| 4,666,437 A | 5/1987 | Lambert | |
| 4,979,939 A | 12/1990 | Shiber | |
| 5,304,189 A | 4/1994 | Goldberg et al. | |
| 5,360,003 A | 11/1994 | Capistrano | |
| 5,423,331 A | 6/1995 | Wysham | |
| 5,634,475 A * | 6/1997 | Wolvek | 600/585 |
| 5,634,935 A | 6/1997 | Taheri | |
| 5,695,514 A | 12/1997 | Chin | |
| 5,968,066 A | 10/1999 | Fogarty et al. | |
| 6,022,313 A | 2/2000 | Ginn et al. | |
| 6,033,414 A * | 3/2000 | Tockman et al. | 606/129 |
| 6,080,175 A | 6/2000 | Hogendijk | |
| 6,143,008 A | 11/2000 | Eaves | |
| 6,193,653 B1 | 2/2001 | Evans et al. | |
| 6,512,959 B1 * | 1/2003 | Gomperz et al. | 607/122 |
| 6,818,003 B2 | 11/2004 | Genovesi | |
| 7,004,926 B2 | 2/2006 | Navia et al. | |
| 2005/0004421 A1 | 1/2005 | Pacella et al. | |
| 2005/0004586 A1 | 1/2005 | Suval | |

FOREIGN PATENT DOCUMENTS

| | | |
|---|---|---|
| DE | 197 54 779 A1 | 6/1999 |
| DE | 198 17 979 A1 | 11/1999 |
| EP | 0 554 754 B1 | 8/1993 |
| GB | 2082 459 A | 3/1982 |

* cited by examiner

*Primary Examiner*—Kevin C Sirmons
*Assistant Examiner*—Andrew M Gilbert
(74) *Attorney, Agent, or Firm*—Fennemore Craig, P.C.

(57) ABSTRACT

A device for gripping a guide wire includes a body portion having an opening therethrough, and has an open position and a closed position. When the device is in the open position the guide wire may be passed through the opening. When the device is in the closed position the guide wire is gripped at more than one location thereby allowing force or torque to be applied to the guide wire. A device according to the invention may optionally, or instead, include (a) a snout to act as a guide wire director, (b) a structure, such as an opening, configured to receive an end of a guide wire package, (c) a structure for securing a body member to the device, and/or (d) a mechanism for advancing or retracting a guide wire. If the device includes one of these optional features, it need not be designed to grip a guide wire at two or more locations.

37 Claims, 9 Drawing Sheets

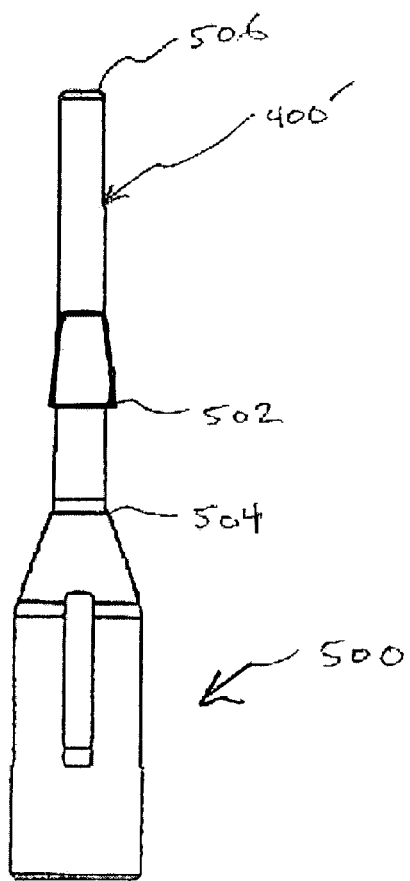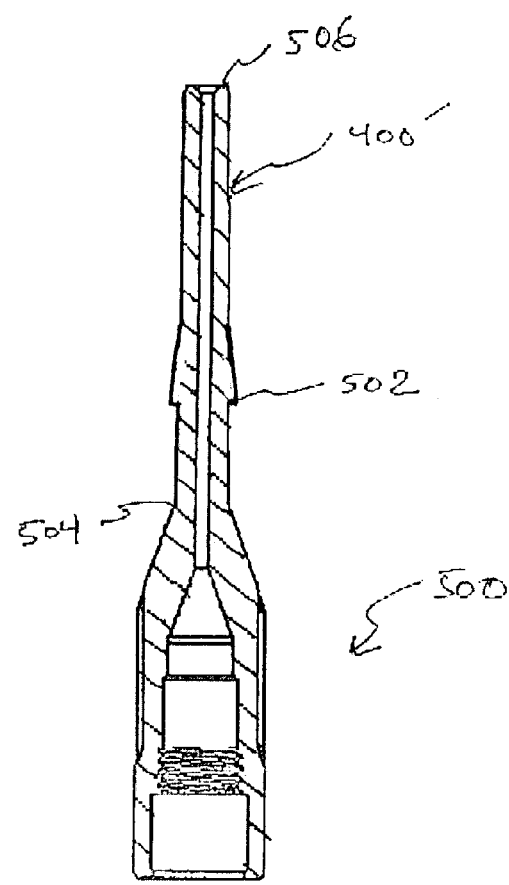
Fig. 5
Fig. 5A

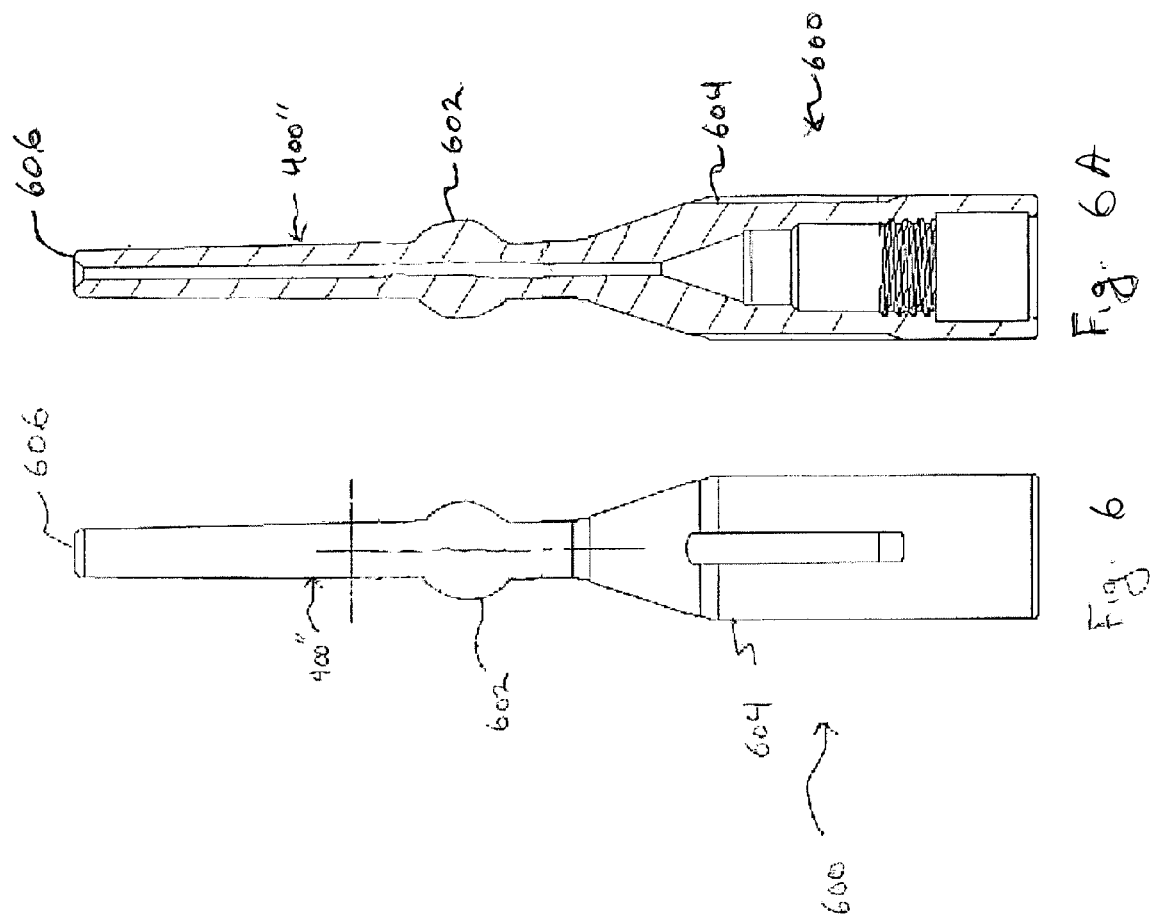

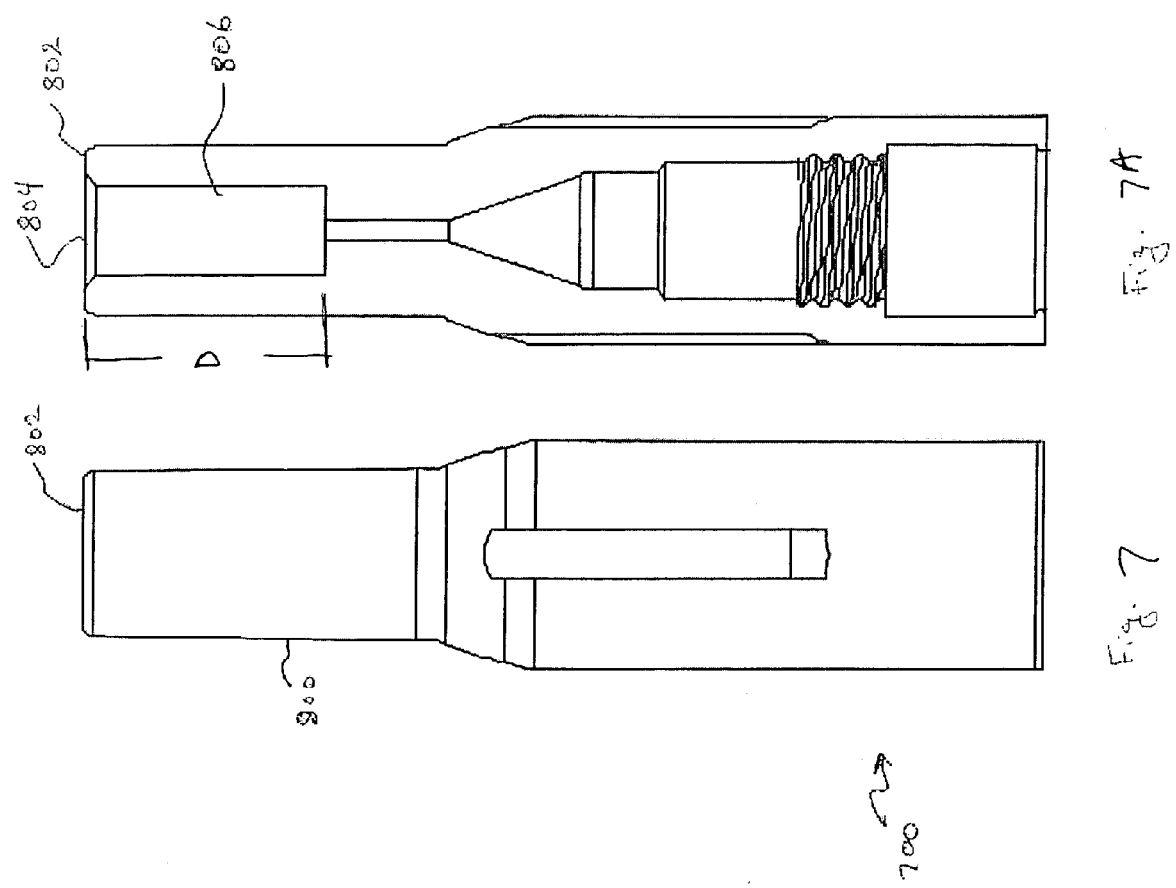

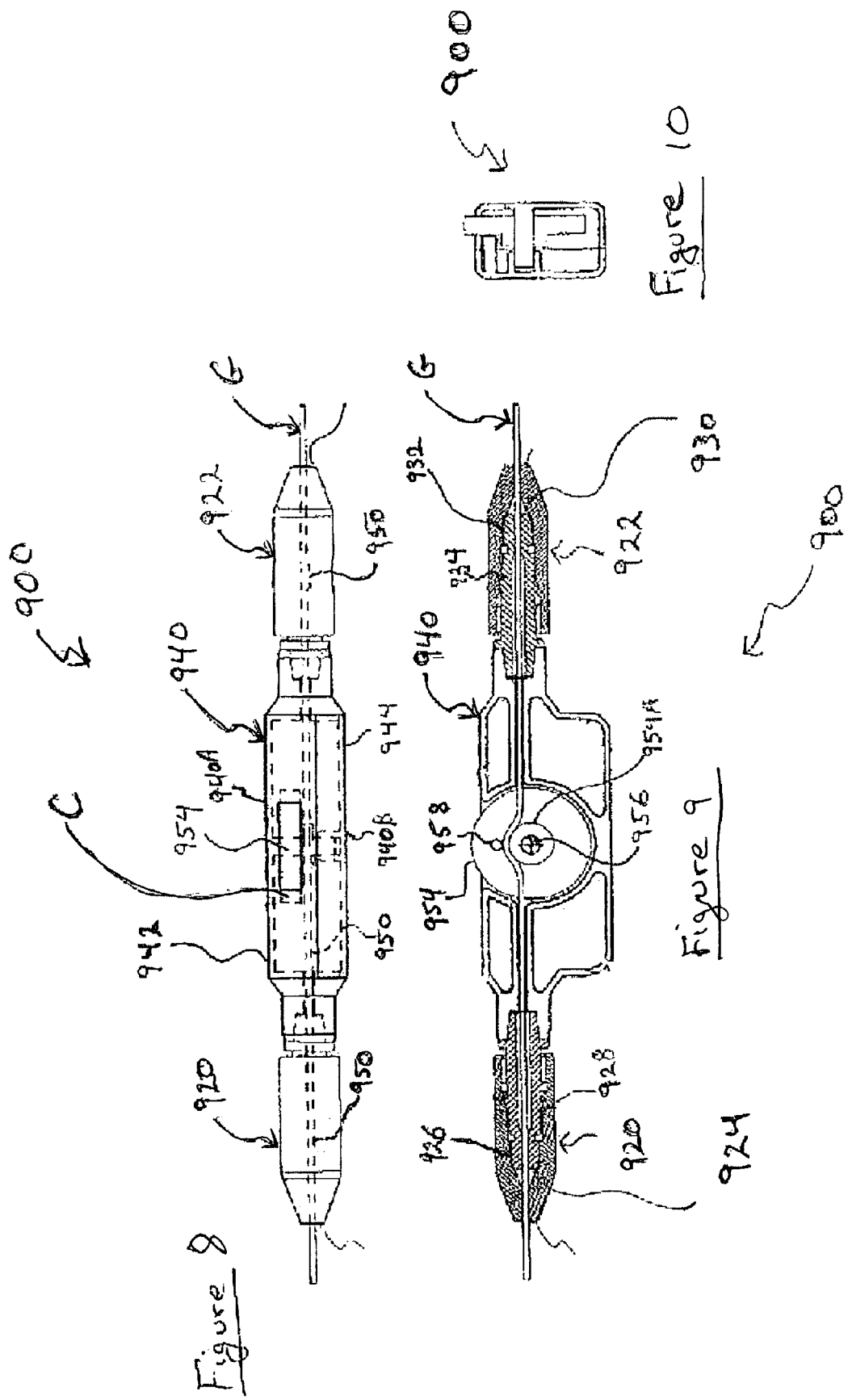

GUIDE WIRE TORQUE DEVICE

TECHNICAL FIELD OF THE INVENTION

This invention relates to a device for gripping a guide wire in a manner such that torque and/or force can be applied to the guide wire to direct it during a medical procedure.

BACKGROUND OF THE INVENTION

Certain medical procedures include the use of a guide wire that is passed through one or more tubular vessels in the body, such as blood vessels. Among these procedures are (a) percutaneous transluminal coronary angioplasty (PCTA), wherein a balloon catheter is steered through a blood vessel to a given location and inflated in order to dilate a coronary artery, (b) stent or stent graft insertion, (c) blood vessel stripping. (d) blood vessel harvesting, (e) angiography, and (t) percutaneous transluminal angioplasty.

For procedures involving a blood vessel the guide wire is typically introduced into a vessel via an opening made by a surgeon. For example, a guide wire may be introduced through a small needle hole made in the femoral artery in the groin area. The guide wire may then be maneuvered through the femoral artery and aorta and into branches of the vascular system until it reaches the desired location in the desired vessel. Maneuvering the guide wire requires the surgeon to apply torque to the end of the wire outside of the body (the "proximal end") to twist or rotate the wire, thereby changing the position of the end of the wire inside the body (the "distal end") to guide it into openings to branch vessels.

Guide wires often have a slippery, hydrophilic coating to provide high lubricity thus allowing the wire to pass easily through an organ, such as a blood vessel. However, such guide wires may be so slippery that sufficient torque cannot be applied by simply rolling or twisting the proximal end of the guide wire between a thumb and forefinger. Consequently, a torque device is needed to grip the guide wire for adequate torque to be applied.

Traditional torque devices are comprised of a small tube, or body portion, having an opening therethrough. At one end of the tube is a structure, such as a collect having four fingers that can be pressed together to grip the guide wire. A screw cap having a hole for the passage of the guide wire therethrough is secured to the tube, is positioned over the collet and has a tightened position and a loosened position. As the cap is moved to the tightened position, the fingers are compressed radially inward, gripping the guide wire positioned between them. The guide wire can then be manipulated by turning or twisting the torque device.

A drawback of known torque devices is that the guide wire can only be threaded from one end, i.e., through the cap positioned at one end of the torque device, which may make the device difficult to thread in the operating room. Additionally, known torque devices grip a guide wire at just one location, which does not always sufficiently secure the guide wire to allow the application of adequate torque and/or force for steering or to pull the guide wire taut during certain procedures, such as vein harvesting (during which, additional longitudinal displacement forces may be encountered). Additionally, with known torque devices the guide wire must be advanced or retracted by holding the guide wire in one hand, which can be awkward.

In addition, guide wires are packaged for shipping. A commonly-used guide wire package is a tubular plastic sheath into which the guide wire is placed. Typically, when packaged, an end of the guide wire extends outside of an end of the package and a guide wire director is positioned on the exposed end of the guide wire. The guide wire director has a first end that includes an opening dimensioned to receive the end of the guide wire package, thus securing the director and guide wire during shipping and handling, and a second end that includes an elongated snout, which is used to introduce the guide wire into a lumen, such as the lumen of a vein or catheter. It would be advantageous to provide a torque device that could be preapplied to the guide wire (rather than being applied in the operating room) and that could be positioned on an end of a guide wire package so it remained positioned thereon during shipping. It would also be advantageous if a torque device included a snout to assist in introducing a guide wire into a lumen.

SUMMARY OF THE INVENTION

One device according to the invention is a guide wire torque device for gripping a guide wire at more than one location on the wire. The torque device has an opening extending therethrough, an open position and a closed position. When the torque device is in the open position the guide wire may be passed through the opening. When the device is in the closed position the guide wire is gripped at more than one location thereby allowing torque and/or force to be applied to the guide wire.

One preferred embodiment of the torque device described above includes a body portion, a first cap secured to a first end of the body portion and a second cap secured to a second end of the body portion. The opening extends through the body portion. A first collet is formed at the first end of the body portion and a second collet is formed at the second end of the body portion. Each collet includes a plurality of compressable fingers for gripping a guide wire, however, any structure(s) for gripping a guide wire may be used. The first cap engages the first collet and may be tightened to the first end of the body portion, preferably by utilizing a threaded connection. When tightened, the first cap compresses the fingers of the first collet so that the fingers grip the guide wire. The second cap engages the second collet and may be tightened to the second end of the body portion, also preferably by utilizing a threaded connection. When tightened, the second cap compresses the fingers of the second collet so the fingers of the second collet grip the guide wire.

An alternate torque device according to the invention includes an elongated snout (or simply "snout"), to assist in straightening and/or guiding a guide wire, such as an angled or J-tipped guide wire, into a lumen, such as the lumen of a vein or a cannula, and thus acting as a guide wire director. Such a device is configured to grip a guide wire at one or more locations when in the closed position.

Another torque device according to the invention is configured to receive the end of a guide wire package. Such a torque device is preferably mounted to a guide wire extending outside the end of the package and the torque device is positioned so that the end of the guide wire package is received in an opening in the torque device. This secures the torque device to the guide wire package during shipping to help protect the guide wire and the torque device. Such a torque device is configured to grip a guide wire at one or more locations when in the closed position.

A torque device according to the invention may also include a structure for securing a body member (such as a blood vessel) or other object to the device, the structure preferably being an annular bump or ridge, wherein the ridge is preferably positioned on an elongated snout of the device.

Another torque device according to the invention includes a mechanism, such as a thumb wheel, for advancing or retracting a guide wire. Such a device may further include an elongated snout, a structure for securing a body member or other object thereto, and grips a guide wire at one or more locations when in the closed position. In this embodiment the guide wire may be gripped solely by the mechanism or by the mechanism and other structures on the device.

Another device according to the invention includes an opening in the body portion of the device that exposes a guide wire contained therein. The exposed guide wire can then be advanced or retracted utilizing one's finger or thumb.

BRIEF DESCRIPTION OF THE DRAWINGS

A detailed description of the invention will be made with reference to the accompanying drawings wherein:

FIG. 5 is a side view of another alternate cap to be used with a device according to the invention wherein the cap includes a structure for securing a body member or other object thereto.

FIG. 5A is a cross-sectional view of the cap shown in FIG. 5.

FIG. 6 is a side view of another alternate cap to be used with a device according to the invention wherein the cap includes a snout and an alternate structure for securing a body member or other object thereto.

FIG. 6A is a cross-sectional view of the cap shown in FIG. 6.

FIG. 7 is a side view of another alternate cap that may be used with a device according to the invention, wherein the cap has an opening dimensioned to receive a guide wire package.

FIG. 7A is a cross-sectional view of the cap shown in FIG. 7.

FIG. 8 is a top view of an alternate device according to the invention, wherein the device includes a mechanism for advancing or retracting a guide wire.

FIG. 9 is a cross-sectional view of the device of FIG. 8.

FIG. 10 is an end view of the device of FIG. 8.

DETAILED DESCRIPTION OF A PREFERRED EMBODIMENT

Figure 1:
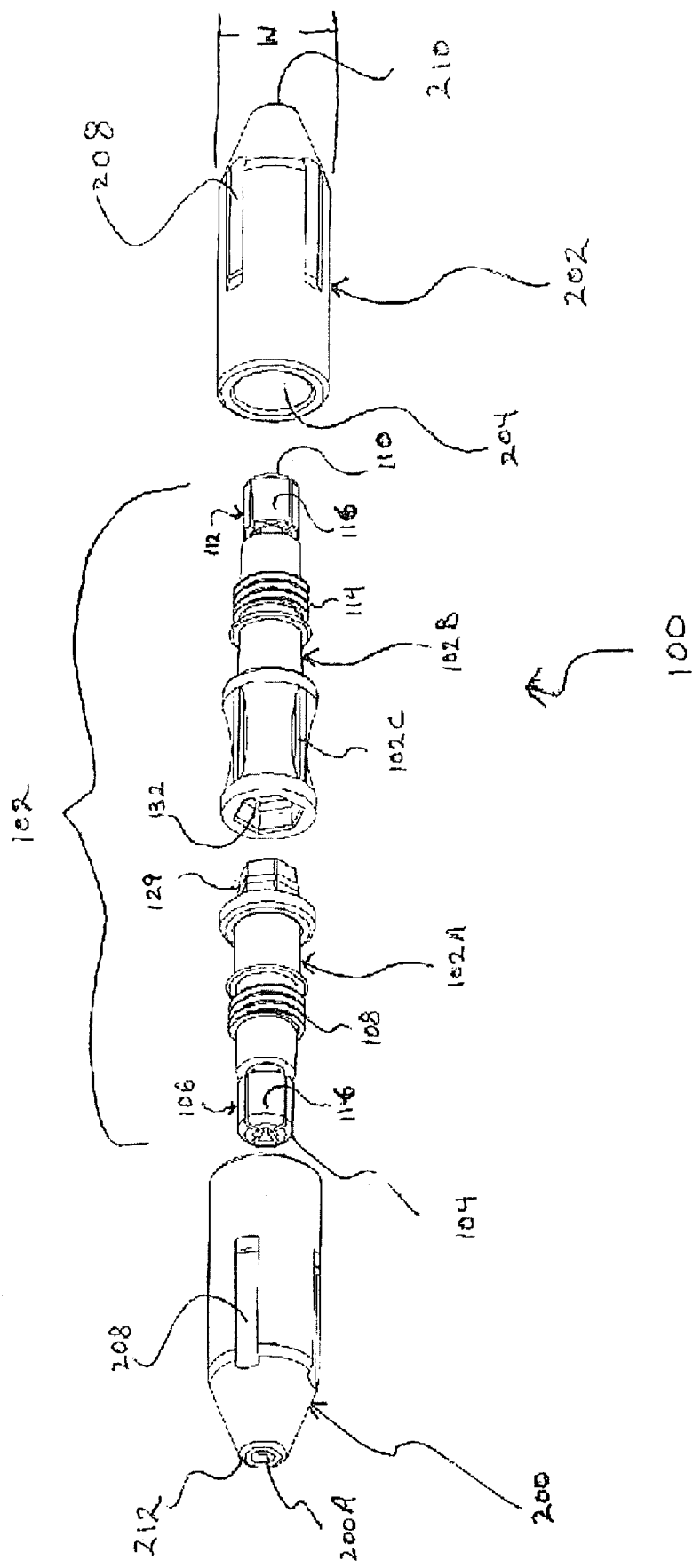
FIG. 1 is a peripheral, exploded view of a preferred embodiment of one aspect of the present invention.
Figure 2:
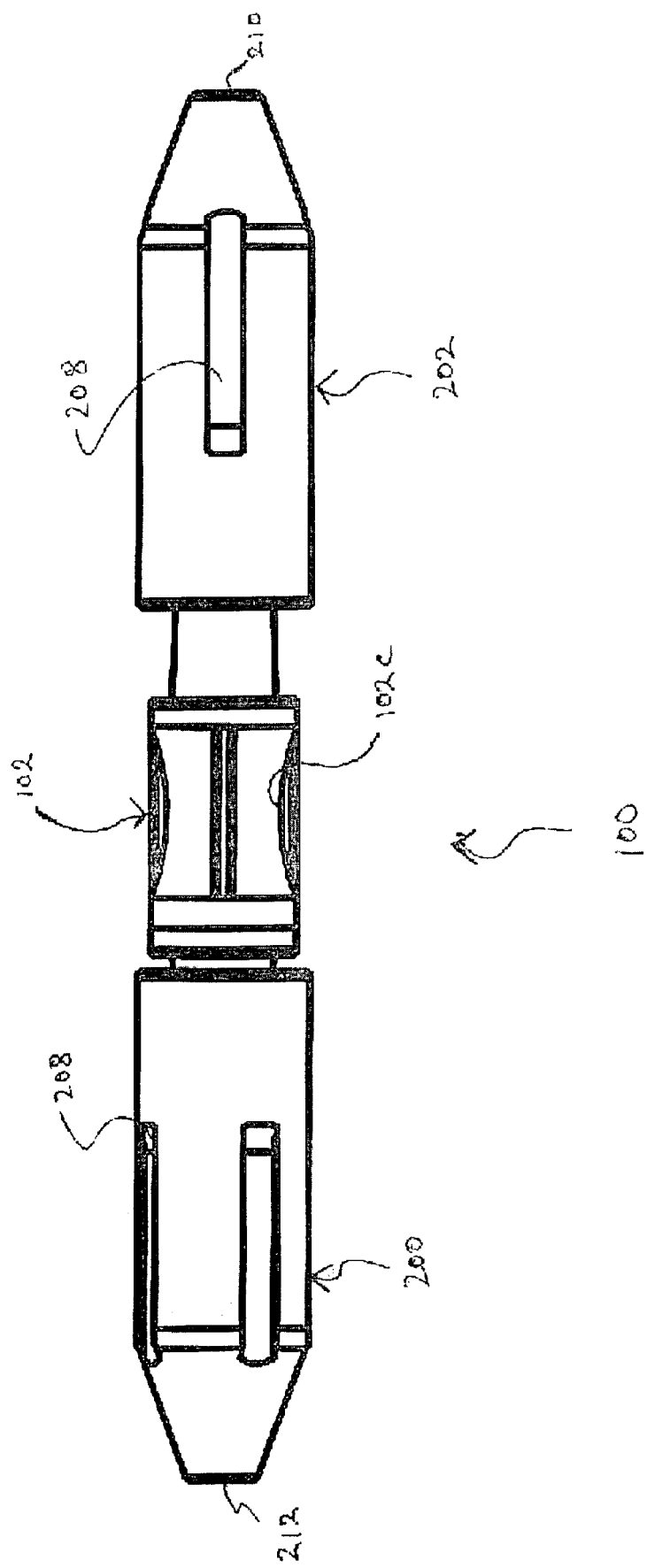
FIG. 2 is a side view of the device shown in FIG. 1 with the components assembled.
Figure 3:
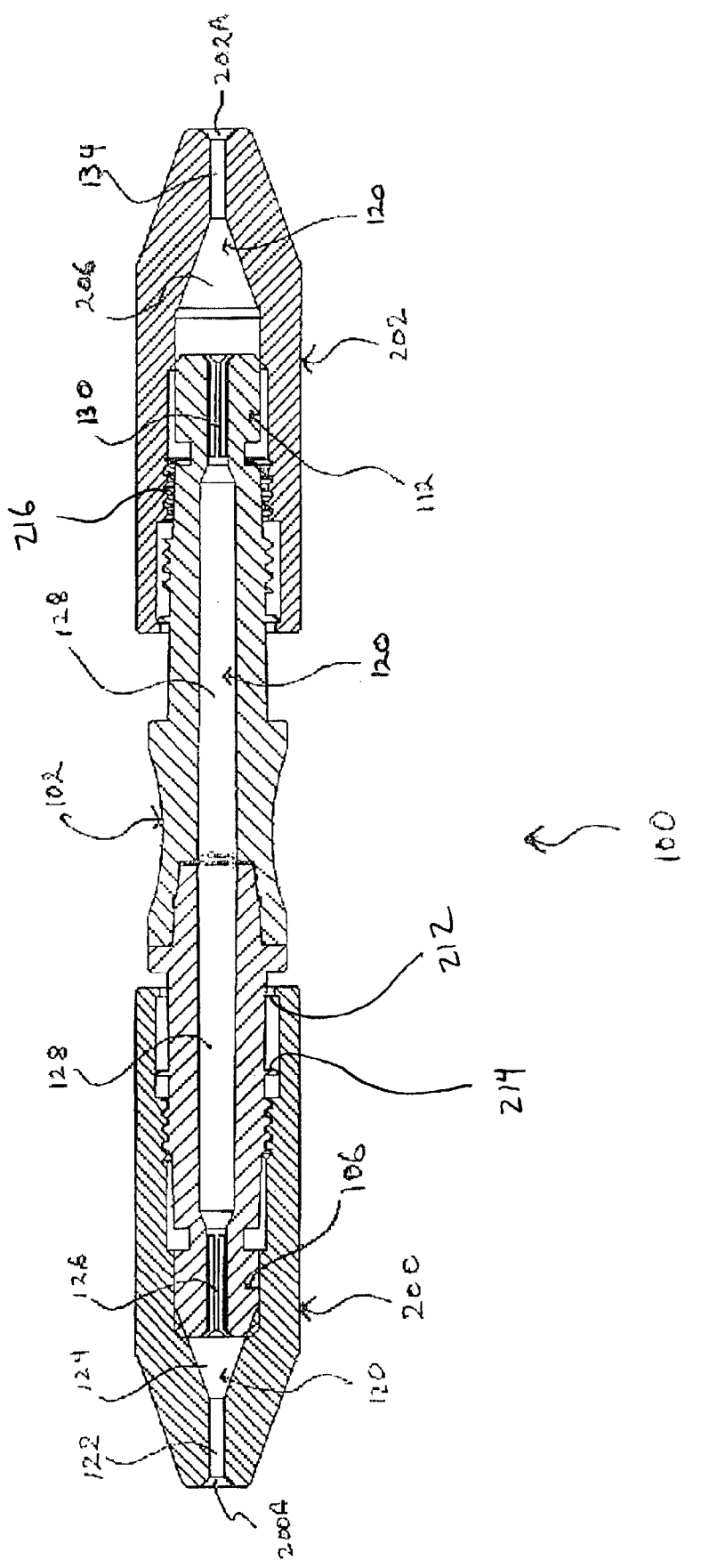
FIG. 3 is a cross-sectional view of the device shown in FIG. 2.

Turning now to the drawing where the purpose is to describe preferred embodiments of the invention and not to limit same, a preferred embodiment of one aspect of the invention is device 100, illustrated in FIGS. 1-3. Device 100 is for gripping a guide wire (not shown) used in medical procedures and for allowing a user (typically a surgeon, cardiologist or radiologist) to provide torque and/or force to the guide wire. Device 100 is preferably comprised of plastic such as polypropylene or acetal (including AMILUS acetal, supplied by Southland Polymers Inc., 14030 Gannet St., Santa Fe Springs, Calif. 90670) or other suitable plastic or other material and preferably has a maximum width W of 9 mm or less.

Device 100 comprises a body portion 102 preferably comprised of a first section 102A and a second section 102B that snap fit or pressure fit together, although any method of attachment may be used. Body portion 102 could be comprised of a single section or any number of sections; the preferred embodiment of body portion 102 includes two sections for ease of manufacturing. In the preferred embodiment, section 102A has a length of about 27 mm and section 102B has a length of about 34 mm, although any suitably-sized body portion and/or body potion sections may be used.

Body portion 102 may include one or more handling surfaces 102C. Each handling surface 102C assists in the handling and manipulation of device 100 and may be a raised section on body portion 102, a series of grooves or depressions formed in body portion 102 or any structure formed on body portion 102 that allows for easier handling and manipulation by a user.

Body portion 102 includes a first end 104 that has a collet 106 and a threaded portion 108. Body portion 102 also includes a second end 110 that has a collet 112 and a threaded portion 114. Each collet 106, 112 includes multiple (four are shown in the drawing) longitudinally-extending and substantially parallel projections or fingers 116. In the preferred embodiment, each of fingers 116 has a cross-section approximately resembling ¼ of a circle. Although the preferred embodiment shows fingers, any structure(s) on the torque device suitable for performing the gripping function may be used. Further, if fingers are used to grip the guide wire, any number of fingers of any shape can, be employed as long as they can grip a guide wire when compressed.

As shown in FIG. 3, on opening 120 is defined through body portion 102, and opening 120 comprises interconnected openings 122, 124, 126, 128, 130, 206 and 134. Opening 120 is designed to be sufficiently large enough to allow the guide wire (a typical guide wire has a diameter of between 0.010 to 0.038 inches) used with device 100 to be inserted through device 100 when device 100 is in the open position (as described below) and the width or diameter of opening 120 may vary along its length. Openings 126, 130 in collets 106, 112, respectively, are preferably substantially the same size. As used herein, substantially the same size means that the collets (or any gripping structure(s) used to practice the invention) have openings and appropriate structure such that they each grip the same guide wire when compressed. In one preferred embodiment each collet 106, 112 has an outside diameter of 4.75 mm and openings 126, 130 each have a diameter of 0.94 mm when fully open (i.e., when not compressed), although the invention is not limited to these dimensions and an opening through which the guide wire passes need not be cylindrical.

In the embodiment shown, body portion 102 includes a projection 129 and a cavity 132. Projection 129 is received in cavity 132, preferably in a snap-fit manner, to connect sections 102A and 102B.

Device 100 also includes a first cap 200 and a second cap 202 that are each preferably secured to body portion 102 to allow for easier handling of device 100 than having the caps completely separate from the body portion, in which case device 100 would comprise multiple, loose pieces. (However, one or more caps used with a device according to the invention could not be secured to the body portion.) Cap 200 is secured to body portion 102 via any suitable means, such as an ultrasonic weld, or a snap-fit (or pressure fit) connection wherein a raised annular ring inside cap 200 is pressed past a raised annular ring on end 104. This secures cap 200, but does not tighten it to, body portion 102. Cap 202 is secured to second end 110 in the same manner.

In this embodiment, first cap 200 and second cap 202 have the same structure so only cap 202 shall be described in detail. Cap 202 has an opening 204 leading to a tapered, inner cavity 206 (shown in FIG. 3), and further includes threads in cavity 206. Cap 202 also includes a tip 210 having an opening 202A through which the guide wire can pass and cap 200 includes a tip 212 having an opening 200A through which the guide wire can pass. First cap 200 and/or second cap 202 may also include one or more cap handling surfaces 208 to assist in tightening and loosening each or either of the caps to body portion 102. Each handling surface 208 can be any structure suitable for this purpose. Cap 200 is tightened to body portion 102 by screwing it onto threaded portion 108. Cap 202 is tightened to body portion 102 by screwing it onto threaded portion 114.

While caps 200, 202 are shown as screw-on caps, other methods of tightening first cap 200 and second cap 202 to body portion 102 may be used as long as the respective cap, when tightened to body portion 102, compresses the plurality of fingers on the respective collet 106, 112 with which the cap is associated to grip a guide wire. For example, one or both caps may snap onto body portion 102, or the caps may be non-removable screw-on or snap-on chucks that compress the fingers when tightened. Additionally, as previously stated, a device according to the invention may use any suitable structure for gripping a guide wire; it need not use collets and caps.

Device 100 is in the open position when first cap 200 and second cap 202 are loosened sufficiently (i.e., are each in the loosened position), such that a guide wire may be fed through one of the cap openings 200A or 202A, through opening 120 and out the other cap opening 200A or 202A. Device 100 is in the closed position when caps 200, 202 are tightened, causing the fingers of the first collet 106 and the fingers of the second collet 112 to radially compress such that the collets compress against any guide wire present, thereby applying pressure to and gripping the guide wire at two locations (as used herein, "location" means any separate point or area of contact on a guide wire). First cap 200 and second cap 202 may be tightened or loosened in any order, or may be loosened or tightened simultaneously. As shown in FIG. 3, cap 200 is in the tightened position and cap 202 is in the loosened position.

When a guide wire is positioned in device 100 and device 100 is in the closed position, device 100 can be manipulated by a surgeon or other user to provide torque and/or force to the guide wire. Handling surfaces 102C and/or 208, if used, assist in the manipulation of device 100. By manipulation of device 100 the guide wire can be steered into and passed through blood vessels or other body structures. Device 100 may also be used to manipulate a guide wire when only gripping the guide wire at one location, but it is preferred that device 100 be used by gripping a guide wire at more than one location in which case greater torque may be applied to the guide wire.

Therefore, device 100 can grip a single guide wire at more than one location. By gripping the guide wire at more than one location, the guide wire is held more securely and greater torque (and hence greater or easier manipulation of the guide wire through a blood vessel) or force can be transmitted to the wire. Gripping the wire at more than one location also yields the added benefit of reduced potential to damage the wire's coating due to load sharing between the multiple locations. Also, in the preferred embodiment of the present invention, having a cap on each side of the device, the guide wire can be easily inserted through either side of the device.

Figure 4:
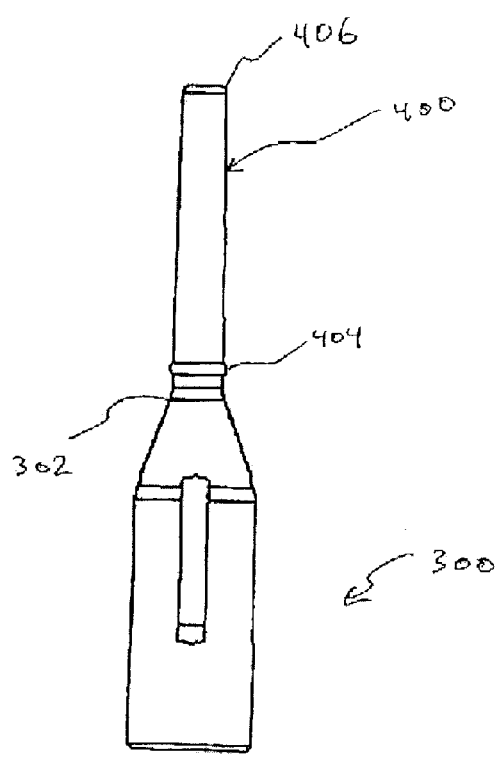
FIG. 4 is a side view of an alternate cap that may be used with a device according to the invention wherein the cap includes a snout and a structure for securing a body member or other object thereto.
Figure 4A:
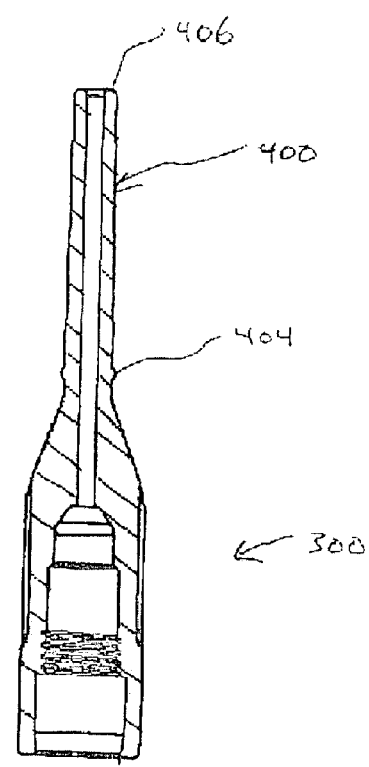
FIG. 4A is a cross-sectional view of the cap shown in FIG. 4.

FIGS. 4 and 4A show an alternate cap 300 that can also be used to practice the invention. A cap 300 may be used with body portion 102 in place of cap 200 and/or a cap 300 may be used in place of cap 202. Cap 300 includes a snout 400 that extends from a base portion 302. Snout 400 includes a structure 404 for securing a body portion (such as a blood vessel) or other object to cap 300 and a tip 406. In this embodiment, structure 404 comprises an annular bump and a body portion or other object is preferably attached to cap 300 via a suture ligature between structure 404 and base 302. In all other respects, a device utilizing body portion 102 and one or two caps 300 is the same as previously described device 100.

The purpose of snout 400 (and snouts 400' (shown in FIGS. 5 and 5A) and 400" (shown in FIGS. 6 and 6A) described below) is to assist the surgeon in introducing a guide wire into a lumen, such as the lumen of a blood vessel or cannula (particularly the cannula of a luer lock). Any snouts according to the invention must only be sufficiently long and narrow for this purpose. In the preferred embodiment snout 400 (and all snouts described herein) is preferably between ½"-1¼" in length from the base (here, base 302) to the tip (here, tip 406) and is most preferably about ¾" in length (with one embodiment being 0.754" in length). The outside diameter of tip 406 (and the tips of all snouts herein) is preferably less than 4.5 mm and most preferably about 0.94". However, the invention is not limited to these specific dimensions.

FIGS. 5 and 5A show a cap 500 that can be used to practice the invention. A cap 500 may be used with body portion 102 in place of cap 200 and/or a cap 500 may be used in place of cap 202. Cap 500 has a snout 400' (that as shown has the same configuration as snout 400) and includes a structure 502 for securing a blood vessel or other object to cap 500, preferably with a suture ligature, a base 504 and a tip 506. As shown, structure 502 is an annular ridge, but may be any suitable structure formed on or attached to cap 500 for securing a body member or other object to cap 500. In all other respects, a device utilizing body portion 102 and one or two caps 500 is the same as previously described device 100.

FIGS. 6 and 6A show a cap 600 that can be used to practice the invention. Cap 600 has a snout 400" (that as shown has the same structure as snout 400) a structure 602 for securing a blood vessel or other object to cap 600, a base 604 and a tip 606. As shown, structure 602 is a bulb formed in snout 400". A cap 600 may be used in place of cap 200 and/or a cap 600 may be used in place of cap 202. In all other respects, a device utilizing body portion 102 and one or two caps 600 is the same as previously described device 100.

Structure 404, 502 or 602 is designed to assist in securing a suture ligature to cap 300, 500 or 600, respectively, in order to secure a body member (such as a blood vessel) or other object to a device according to the invention, particularly to assist in the removal of a blood vessel in a vein or artery harvesting procedure. However, any object may be secured to a device according to the invention for any reason and, as used herein, the expression "secure a body member" includes both body members and other objects. Any suitable structure may be formed on or mounted to a device according to the invention for that purpose. In the vein harvesting procedure, securing a blood vessel to a device according to the invention may be done prior to straightening the blood vessel. Generally, to straighten a blood vessel, the blood vessel is first accessed at two positions, then a guide wire is fed through the blood vessel and is exposed at both positions, which are called proximal and distal positions. When harvesting a blood vessel, a torque device according to the invention is placed on the guide wire at the proximal position outside of the blood vessel and another device according to the invention is placed on the distal position outside of the blood vessel. An intravascular catheter is passed over the guide wire and through the accessed portion of the blood vessel thus supporting the blood vessel. The blood vessel is then secured to a structure 404, 502, or 602 by a suture ligature and the guide wire, catheter and vessel are pulled straight by applying force to a device to which one or more caps 300, 500 or 600 are attached.

FIGS. 7 and 7A show another alternative cap 700 that can be used with a device according to the invention, wherein the cap can receive the end of a guide wire package. A cap 700 may be used in place of cap 200 and/or a cap 700 may be used in place of cap 202 on body portion 102. As known to those skilled in the art, guide wires are typically packaged in tubular plastic sheaths. Cap 700 has a wide, blunt snout 800 and includes a tip 802 having an opening 804 that leads to cavity 806. Opening 804 and cavity 806 are dimensioned to receive the end of a guide wire package (not shown). Opening 804 and cavity 806 can be of any configuration suitable for receiving the end of a guide wire package so that a torque device utilizing cap 700 remains mounted on the guide wire package during shipping without causing significant damage to the guide wire. This helps to prevent the guide wire or the device from being damaged during shipping or handling. Opening 804 and cavity 806 dimensioned according to the guide wire package they are to receive, but in two embodiments cavity 806 is cylindrical and has diameters of 0.118" and 0.154", respectively. In these embodiments, the depth D of cavity 806 is at least as deep as the diameter of cavity 806, preferably greater than twice as deep as the diameter of cavity 806 and most preferably about 2½ times the diameter of cavity 806. Furthermore, cap 700 may include a structure for securing a blood vessel or other object thereto. In all other respects, a device utilizing body portion 102 and one or two caps 700 is the same as previously described device 100.

It will be understood that, although a torque device according to the invention could include two caps 300, or two caps 500, or two caps 600, it is preferred that a device according to the invention, if it includes one of these caps, only include one. Since these caps each include a snout for directing a guide wire into a lumen, there likely would only be a need for only one at one end of a torque device. Further, while a torque device according to the invention could include two caps 700, it is preferred that, if a torque device includes a cap 700, only one cap 700 be used because only one end of the torque device would be secured to a guide wire package for shipping.

Any of caps 300, 500, 600 or 700 may include one or more of the previously described handling surfaces 208. Furthermore, if a device according to the invention utilizes a cap 300, 500, 600 or 700, it need only include one guide wire gripping structure, such as a single one of the previously described collets or any other suitable structure for gripping a guide wire. In that case, a body portion with which one or more of caps 300, 500, 600 or 700 is used may still have two caps, but at least one of the caps would not assist in compressing the guide wire. Additionally, a device according to the invention, if it includes two caps, may have any combination of caps 200, 300, 500, 600 and 700. For example, a device may have body portion 102, a cap 300 and a cap 700, and one or both of the caps could function with a collet or other structure to grip a guide wire. Moreover, a snout, a structure for securing a body part or other object to a device according to the invention, or an opening or other structure for receiving or connecting to the end of a guide wire package could be formed in the body portion of the device rather than in a cap. In that case, the body portion would still have one or more structures for gripping a guide wire and could still optionally have at least one of the previously described caps. For example, a torque device may have a body portion that includes only a single wire gripping structure, such as a collet, a cap 300 that functions with the collet to grip a guide wire, and an opening formed in the body portion opposite cap 300 wherein the opening is dimensioned to receive an end of a guide wire package.

Turning now to FIGS. 8-10, an alternate device 900 is shown. Device 900 includes two caps 920 and 922 and a body portion 940. Body portion 940 may include one or more gripping structures. If included, the gripping structures would assist in the gripping and manipulation of device 900 in the same manner as described with respect to device 100.

Body portion 940 includes a first end 924 that has a collet 926 and a threaded portion 928, and first end 940 as shown has the same structure and function as previously described first end 104. Body portion 940 also includes a second end 930 that has a collet 932 and a threaded portion 934. As shown second end 930 has the same structure and function as previously described second end 110.

As shown in FIG. 8, an opening 950 is defined through body portion 940, and is designed to be sufficiently large enough to allow the guide wire used with device 900 to be inserted through it when device 900 is in the open position.

Body 940 is preferably formed in two pieces, 940A and 940B that are pressure fit together, although any method of attachment may be used and body 940 may be formed of any number of pieces. A cavity C is defined within body 940. A thumb wheel 954 is positioned partially inside cavity C and extends through an opening (shown here as a slot) in the outer surface of body 940. Drive wheel 954A is integrally formed with or is attached to thumb wheel 954. Thumb wheel 954 is mounted on an axle 956 such that it can be rotated. An idler 958 is mounted to or integrally formed as part of section 940A so that a gap is formed between drive wheel 954A and idler 958. The gap is of sufficient distance to allow the guide wire G to pass through it while still providing for a pressure fit between idler 958 and drive wheel 954A to enable guide wire G to be advanced or retracted by moving thumb wheel 954, which in turn moves drive wheel 954A. The purpose of thumb wheel 954, drive wheel 954A and idler 958 is to enable a user to move a guide wire positioned inside device 900 without the user having to grip or handle the guide and any structure in or on device 900 suitable for this purpose may be used.

Device 900 also includes a first cap 920 and a second cap 922 that are each preferably secured to body portion 940 to allow for easier handling than having multiple, loose pieces. In this embodiment, first cap 920 and second cap 922 each have the same structure and function as previously described cap 202. Alternatively, body portion 940 may be used with one or two of caps 300, 500, 600 and/or 700.

A device according to the invention that includes a mechanism for advancing or retracting a guide wire may only include one structure for gripping guide wire G when the device is in the closed position. Alternatively, it may not include any dedicated gripping structures because the pressure between drive wheel 954A and idler 958 may be sufficient to apply torque to the guide wire and direct it. In that case, the mechanism may have an open position in which the guide wire may be threaded through an opening in the mechanism larger than the guide wire, and a closed position wherein pressure is applied by the mechanism to grip the wire. Alternatively, the mechanism may have a single position and the guide wire may be threaded through the mechanism by advancing it using the mechanism. For example, referring to the mechanism shown as the preferred embodiment, the guide wire may be threaded up to the gap between drive wheel 954A and idler 958 and then thumb wheel 954 may be turned to advance the guide wire through the gap.

Figure 11:
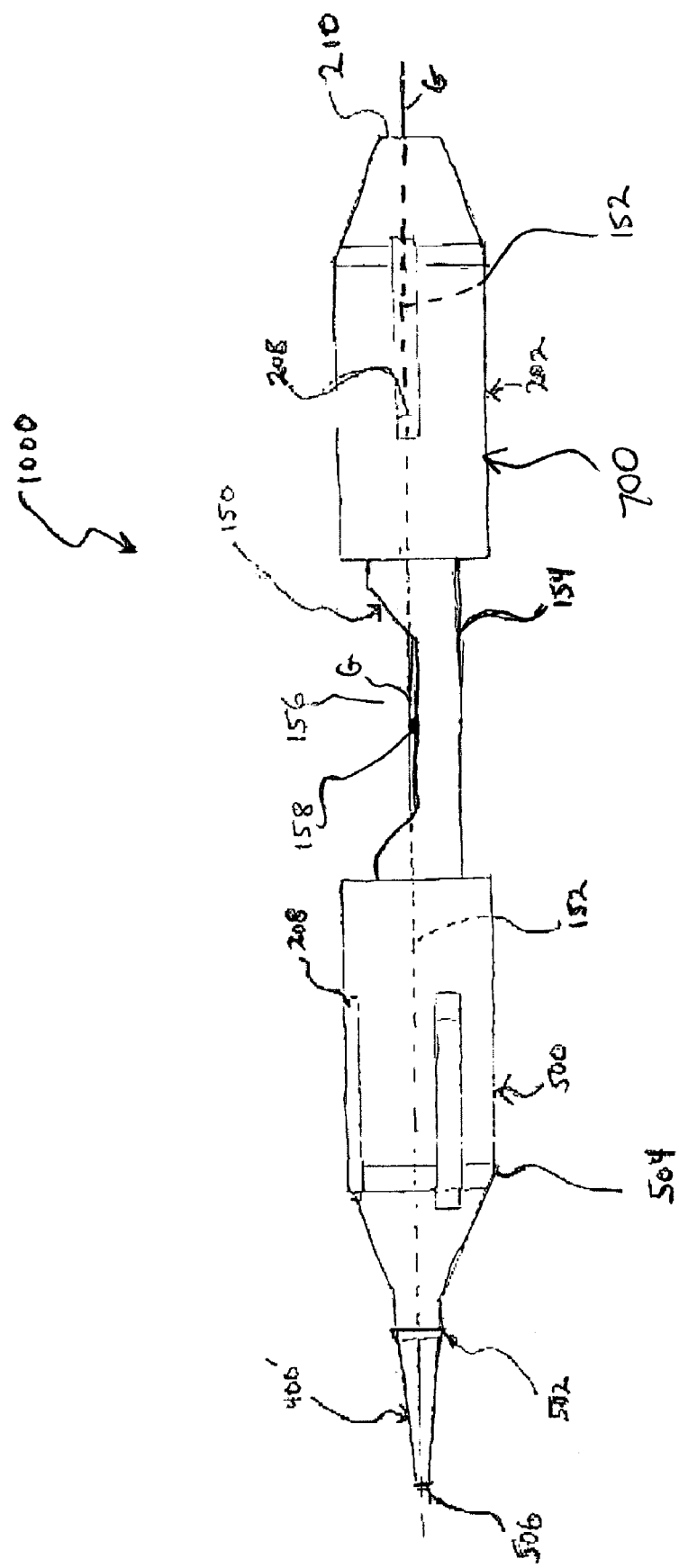
FIG. 11 is a side view of an alternate device according to the invention.

FIG. 11 shows an alternate device 1000 according to the invention. As shown, device includes a cap 500 and a cap 700. Device also includes a body portion 150 that has an opening 152 in which a guide wire G is positioned, a center portion 154 and an opening 156 in center portion 154. The ends of body portion 150, which engage the caps and (in the preferred embodiment) include collets for gripping a guide wire in the manner previously described, preferably have the same structure as those on previously described body portion 102. A bridge 158 is preferably formed in the bottom of opening 156 and is preferably a rounded, smooth ridge that extends substantially the width of opening 156. Opening 156 exposes guide wire G positioned in cavity 152 and a user can advance or retract guide wire G by applying pressure to the exposed guide wire and pressing it against bridge 158. Any structure suitable to create a pressure fit between a user's thumb or finger in order to advance or retract a guide wire may be used in place of bridge 158, and the pressure fit may simply be made between the user's finger and the lower surface of opening 156.

Having thus described different embodiments of the invention, other variations and embodiments that do not depart from the spirit of the invention will become readily apparent to those skilled in the art. The scope of the present invention is thus not limited to any one particular embodiment, but is instead set forth in the appended claims and the legal equivalents thereof.

What is claimed is:

1. A device for gripping a guide wire at more than one location, the device comprising:
   (a) a body portion including:
      (i) a first end, a second end and a substantially uniform opening therethrough;
      (ii) a first collet at the first end of the body portion, the first collet having a plurality of compressible fingers and a first opening therebetween; and
      (iii) a second collet at the second end of the body portion, the second end having a plurality of compressible fingers and a second opening therebetween, the second opening being substantially the same size as the first opening when the plurality of compressible fingers of the first collet is fully compressed and the plurality of compressible fingers of the second collet is fully compressed; and
   (b) a first cap for engaging the first collet and compressing the fingers of the first collet when the first cap is tightened to the body portion, the first cap configured to receive an end of a guide wire package and including an opening through which a guide wire can pass; and
   (c) a second cap for engaging the second collet and compressing the fingers of the second collet when the second cap is tightened to the body portion, the second cap including (i) a snout, (ii) a structure for securing a body part thereto and (iii) an opening through which a guide wire can pass.

2. A device for gripping a guide wire at more than one location, the device comprising:
   (a) a body portion including:
      (i) a first end and a second end;
      (ii) a first collet at the first end of the body portion, the first collet having a plurality of compressible fingers and a first opening therebetween; and
      (iii) a second collet at the second end of the body portion, the second end having a plurality of compressable fingers and a second opening therebetween, the second opening being substantially the same size as the first opening when the plurality of compressible fingers of the first collet is fully compressed and the plurality of compressible fingers of the second collet is fully compressed; and
   (b) a first cap for engaging the first collet and compressing the fingers of the first collet when the first cap is tightened to the body portion and including an opening through which a guide wire can pass; and
   (c) a second cap for engaging the second collet and compressing the fingers of the second collet when the second cap is tightened to the body portion, the second cap including an opening through which a guide wire can pass.

3. The device of claim 2 wherein one of the caps includes an opening dimensioned to receive an end of a guide wire package.

4. The device of claim 2 that further comprises an elongated snout.

5. The device of claim 4 wherein the snout is formed in one of the caps.

6. The device of claim 2 that further includes a structure for securing a body member to the device.

7. The device of claim 2 that is comprised of plastic.

8. The device of claim 2 wherein the body portion further comprises threads on the first end juxtaposed the first collet, and the first cap includes an opening having threads, the threads in the opening receiving the threads on the first end to tighten the first cap to the body.

9. The device of claim 2 wherein the body portion further comprises threads on the second end juxtaposed the second collet, and the second cap includes an opening having threads, the threads in the opening receiving the threads on the second end to tighten the second cap to the body.

10. The device of claim 2 wherein the body portion is manufactured in two pieces.

11. The device of claim 2 wherein the first collet comprises multiple substantially parallel, longitudinally-extending fingers.

12. The device of claim 2 wherein the second collet comprises multiple substantially parallel, longitudinally-extending fingers.

13. The device of claim 2 that includes a cavity dimensioned to receive an end of a guide wire package.

14. A body portion for a device wherein the device is used to grip a guide wire at more than one location, the body portion comprising:
   (a) a first end and a second end;
   (b) a first collet at the first end and a first opening through the first collect, the first collet having an open position and a closed position; and
   (c) a second collet at the second end and a second opening through the second collet, the second collet having an open position and a closed position; wherein the first opening is substantially the same size as the second opening when the first collet and the second collet are each in the closed position.

15. The body portion of claim 14 that is comprised of plastic.

16. The body portion of claim 14 that is manufactured in two pieces.

17. The body portion of claim 14 wherein the first collet comprises multiple substantially parallel, longitudinally-extending fingers.

18. The body portion of claim 14 wherein the second collet comprises multiple substantially parallel, longitudinally-extending fingers.

19. The body portion of claim 14 that has a maximum width of 9 mm or less.

20. A device for gripping a guide wire at more than one location, the device comprising:
(a) a body portion including:
   (i) a first end and a second end;
   (ii) a first collet at the first end of the body portion, the first collet having a plurality of compressible fingers and a first opening therebetween; and
   (iii) a second collet at the second end of the body portion, the second end having a plurality of compressable fingers and a second opening therebetween, the second opening being the same size as the first opening when the plurality of compressible fingers of the first collet is fully compressed onto the guide wire and the plurality of compressible fingers of the second collet is fully compressed onto the guide wire; and
(b) a first cap for engaging the first collet and compressing the fingers of the first collet when the first cap is tightened to the body portion and including an opening through which a guide wire can pass; and
(c) a second cap for engaging the second collet and compressing the fingers of the second collet when the second cap is tightened to the body portion, the second cap including an opening through which a guide wire can pass.

21. The device of claim 20 wherein one of the caps includes an opening dimensioned to receive an end of a guide wire package.

22. The device of claim 20 that further comprises an elongated snout.

23. The device of claim 22 wherein the snout is formed in one of the caps.

24. The device of claim 20 that further includes a structure for securing a body member to the device.

25. The device of claim 20 that is comprised of plastic.

26. The device of claim 20 wherein the body portion further comprises threads on the first end juxtaposed the first collet, and the first cap includes an opening having threads, the threads in the opening receiving the threads on the first end to tighten the first cap to the body.

27. The device of claim 20 wherein the body portion further comprises threads on the second end juxtaposed the second collet, and the second cap includes an opening having threads, the threads in the opening receiving the threads on the second end to tighten the second cap to the body.

28. The device of claim 20 wherein the body portion is manufactured in two pieces.

29. The device of claim 20 wherein the first collet comprises multiple substantially parallel, longitudinally-extending fingers.

30. The device of claim 20 wherein the second collet comprises multiple substantially parallel, longitudinally-extending fingers.

31. The device of claim 20 that includes a cavity dimensioned to receive an end of a guide wire package.

32. A body portion for a device wherein the device is used to grip a guide wire at more than one location, the body portion comprising:
(a) a first end and a second end;
(b) a first collet at the first end, the first collet having a plurality of compressible, substantially parallel, longitudinally-extending fingers and a first opening therebetween; and
(c) a second collet at the second end, the second end having a plurality of compressable, substantially parallel, longitudinally-extending fingers and a second opening therebetween, the second opening being the same size as the first opening when the plurality of compressible fingers of the first collet is fully compressed onto the guide wire and the plurality of compressible fingers of the second collet is fully compressed onto the guide wire.

33. The body portion of claim 32 that is comprised of plastic.

34. The body portion of claim 32 that is manufactured in two pieces.

35. The body portion of claim 32 that has a maximum width of 9 mm or less.

36. The body portion of claim 1, wherein the opening through the body portion is uniform.

37. The body portion of claim 1, wherein the opening through the body portion comprises a substantially uniform cross-section.

* * * * *